United States Patent
Garcia Molina et al.

(10) Patent No.: US 11,964,110 B2
(45) Date of Patent: Apr. 23, 2024

(54) SYSTEMS AND METHODS FOR DELIVERING SENSORY STIMULATION TO FACILITATE RECOVERY

(71) Applicant: KONINKLIJKE PHILIPS N.V., Eindhoven (NL)

(72) Inventors: Gary Nelson Garcia Molina, Madison, WI (US); Boomika Kalyan, Pittsburgh, PA (US); Antonio Aquino, Harrison City, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 36 days.

(21) Appl. No.: 17/129,212

(22) Filed: Dec. 21, 2020

(65) Prior Publication Data

US 2021/0187237 A1    Jun. 24, 2021

Related U.S. Application Data

(60) Provisional application No. 62/953,241, filed on Dec. 24, 2019.

(51) Int. Cl.
  *A61M 21/02*    (2006.01)
  *A61B 5/329*    (2021.01)
  *A61M 21/00*    (2006.01)

(52) U.S. Cl.
  CPC ............. *A61M 21/02* (2013.01); *A61B 5/329* (2021.01); *A61M 2021/0022* (2013.01);
  (Continued)

(58) Field of Classification Search
  CPC .......... A61M 21/02; A61M 2021/0022; A61M 2205/056; A61M 2205/3306;
  (Continued)

(56) References Cited

U.S. PATENT DOCUMENTS

| 4,720,093 A | 1/1988 | Del Mar |
| 2002/0155924 A1* | 10/2002 | Dardik ................ A61B 5/0205 482/1 |

(Continued)

FOREIGN PATENT DOCUMENTS

EP    3352844 A1    8/2018

OTHER PUBLICATIONS

International Search Report and Written Opinion, International Application No. PCT/EP2020/087855, dated Apr. 28, 2021.

(Continued)

*Primary Examiner* — Sunita Reddy

(57) ABSTRACT

The present disclosure pertains to a system for delivering sensory stimulation to a subject, the system comprising: sensors configured to generate output signals indicating physiological parameters of a subject; a sensory stimulator configured to deliver sensory stimulation to the subject; and processors configured to: determine one or more physiological parameters of the subject; determine a target physiological parameter based on the determined one or more physiological parameters; determine one or more stimulation parameters of sensory stimulation to be delivered to the subject based on the target physiological parameter and the determined one or more physiological parameters; and cause the sensory stimulator to deliver the sensory stimulation to the subject based on the determined one or more stimulation parameters.

14 Claims, 5 Drawing Sheets

(52) U.S. Cl.
CPC ............... *A61M 2205/056* (2013.01); *A61M 2205/3306* (2013.01); *A61M 2205/3317* (2013.01); *A61M 2205/3584* (2013.01); *A61M 2205/505* (2013.01); *A61M 2230/06* (2013.01); *A61M 2230/10* (2013.01); *A61M 2230/65* (2013.01)

(58) Field of Classification Search
CPC .. A61M 2205/3317; A61M 2205/3584; A61M 2205/505; A61M 2230/06; A61M 2230/10; A61M 2230/65; A61M 2021/0016; A61M 2021/0044; A61M 2021/0055; A61M 2209/088; A61M 2230/04; A61M 2230/30; A61M 2230/40; A61M 2230/63; A61M 2021/0027; A61M 2230/205; A61B 5/7455; A61B 5/14551; A61B 5/318; A61B 5/1118; A61B 5/021; A61B 5/024; A61B 5/0533; A61B 2503/10; A61B 2505/09; A61B 5/0205; A61B 5/4836; A61B 5/486; A61H 2230/045; A61H 2230/065; A61H 2230/655; A61H 23/0245; A61N 1/0484; A61N 1/322; A61N 1/37282; G16H 10/60; G16H 40/63; G16H 20/30
USPC ...................................................... 600/26–28
See application file for complete search history.

(56) References Cited

U.S. PATENT DOCUMENTS

| | | | |
|---|---|---|---|
| 2013/0226264 | A1 | 8/2013 | Chavan |
| 2016/0042142 | A1* | 2/2016 | Arnold ............... G06Q 10/0639 434/236 |
| 2016/0346501 | A1* | 12/2016 | Hooper ............... A61B 5/02438 |
| 2017/0080234 | A1* | 3/2017 | Gillespie ............ A61N 1/36139 |
| 2018/0036531 | A1* | 2/2018 | Schwarz ................ G16H 20/30 |
| 2018/0250494 | A1* | 9/2018 | Hanbury .............. A61B 5/6803 |
| 2019/0133495 | A1* | 5/2019 | Mann ................... A61B 5/6898 |
| 2019/0209843 | A1 | 7/2019 | Park |
| 2022/0175309 | A1* | 6/2022 | Vardas .................. G16H 50/30 |

OTHER PUBLICATIONS

Anonymous: "Artificial cardiac pacemaker—Wikipedia", Nov. 2019.
Serin, A. et al., "The Therapeutic Effect of Bilateral Alternating Stimulation Tactile Form Technology on the Stress Response", Journal of Biotechnology and Biomedical Science, vol. 1, No. 2, Feb. 2018.
Savin, W.M., Davidson, D.M. & Haskell, W.L., 1982. Autonomic contribution to heart rate recovery from exercise in humans. Journal of Applied Physiology, 53(6), pp. 1572-1575.
Hiraba, H. et al., 2014. Facial vibrotactile stimulation activates the parasympathetic nervous system: Study of salivary secretion, heart rate, pupillary reflex, and functional near-infrared spectroscopy activity. BioMed Research International, 2014.
Hiraba, N.H. et al., 2011. Optimal Vibrotactile Stimulation Activates the Parasympathetic Nervous System. In Advances in Vibration Engineering and Structural Dynamics ciples. pp. 355-369.
Lauer, M.S. et al., 2003. Heart Rate Recovery Immediately After Exercise as a Predictor of Mortality. Journal of Cardiopulmonary Rehabilitation, 20(2), pp. 131-132.
Lehrer, P.M. & Gevirtz, R., 2014. Heart rate variability biofeedback: How and why does it work? Frontiers in Psychology, Jul. 5, pp. 1-9.
Liu, L. et al., 2019. Pharmacological Modulation of Vagal Nerve Activity in Cardiovascular Diseases. Neuroscience Bulletin, 35(1), pp. 156-166. Available at: https://doi.org/10.1007/s12264-018-0286-7.
Serin, A., Hageman, N.S. & Kade, E., 2018. The Therapeutic Effect of Bilateral Alternating Stimulation Tactile Form Technology on the Stress Response. Journal of Biotechnology and Biomedical Science, 1(2), pp. 46-52.
Smets, E., De Raedt, W. & Van Hoof, C., 2018. Into the Wild: The Challenges of Physiological Stress Detection in Laboratory and Ambulatory Settings. IEEE Journal of Biomedical and Health Informatics, (November), pp. 1-12.
Yamaguchi, S. et al., "Assessment of Biological Reaction to Whole Body Vibration Training by Evaluating Changes in Salivary Components and Cutaneous Blood Flow", vol. 6 No. 10, Apr. 2014.

* cited by examiner

SYSTEMS AND METHODS FOR DELIVERING SENSORY STIMULATION TO FACILITATE RECOVERY

CROSS-REFERENCE TO PRIOR APPLICATIONS

This application claims the benefit of U.S. Provisional Application No. 62/953,241, filed on 24 Dec. 2019. This application is hereby incorporated by reference herein.

BACKGROUND

1. Field

The present disclosure pertains to systems and methods for providing sensory stimulation to facilitate recovery.

2. Description of the Related Art

According to the American Council of Exercise (ACE), recovery from exercise is vital for high-level performance and continued improvement. Existing recovery strategies like cold-water immersion, ischemic preconditioning, body massage, stretching, and compression garments do not directly address changes in the autonomic profile of the body and recovery associated with heart rate. Vibratory stimulation devices are known but reliable methods to optimize settings to achieve a desired autonomic nervous system (ANS) effect, e.g. higher parasympathetic activity are not clearly defined. The present disclosure overcomes deficiencies in prior art systems.

SUMMARY

Accordingly, one or more aspects of the present disclosure relate to a system for delivering sensory stimulation to a subject, the system comprising: one or more sensors configured to gene rate output signals indicating one or more physiological parameters of a subject; a sensory stimulator configured to deliver sensory stimulation to the subject; and one or more physical processors operatively connected with the one or more sensors and the sensory stimulator, the one or more physical processors being programmed with computer program instructions which, when executed cause the computer system to: determine one or more physiological parameters of the subject based on the output signals from the sensor. In some embodiments, the one or more physiological parameters include a heart rate or heart rate variability (HRV) level of the subject. The one or more physical processors are configured to determine a target physiological parameter based on the on the determined one or more physiological parameters of the subject; determine one or more stimulation parameters of sensory stimulation to be delivered to the subject based on the target physiological parameter and the determined one or more physiological parameters; and cause the sensory stimulator to deliver the sensory stimulation to the subject based on the determined one or more stimulation parameters.

Another aspect of the present disclosure relates to a method for delivering sensory stimulation to a subject, the method comprising: generating, with one or more sensors, output signals indicating one or more physiological parameters of a subject; determining, with one or more physical processors, one or more physiological parameters of the subject based on the output signals from the sensor, the one or more physiological parameters indicating a heart rate of the subject; determining, with one or more physical processors, a heart rate target based on the on the determined one or more physiological parameters indicating the heart rate of the subject, the heart rate target being lower than the determined heart rate; determining, one or more physical processors, one or more stimulation parameters of sensory stimulation to be delivered to the subject based on the heart rate target and the determined one or more physiological parameters; and causing, with one or more physical processors, a sensory stimulator to deliver the sensory stimulation to the subject based on the determined one or more stimulation parameters.

Still another aspect of the present disclosure relates to a system for delivering sensory stimulation to a subject, the system comprising: means for generating output signals indicating one or more physiological parameters of a subject; means for delivering sensory stimulation to the subject; means for determining one or more physiological parameters of the subject based on the output signals from the sensor, the one or more physiological parameters indicating a heart rate of the subject; means for determining a heart rate target based on the on the determined one or more physiological parameters indicating the heart rate of the subject, the heart rate target being lower than the determined heart rate; means for determining one or more stimulation parameters of sensory stimulation to be delivered to the subject based on the heart rate target and the determined one or more physiological parameters; and means for causing means for delivering sensory stimulation to deliver the sensory stimulation to the subject based on the determined one or more stimulation parameters.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
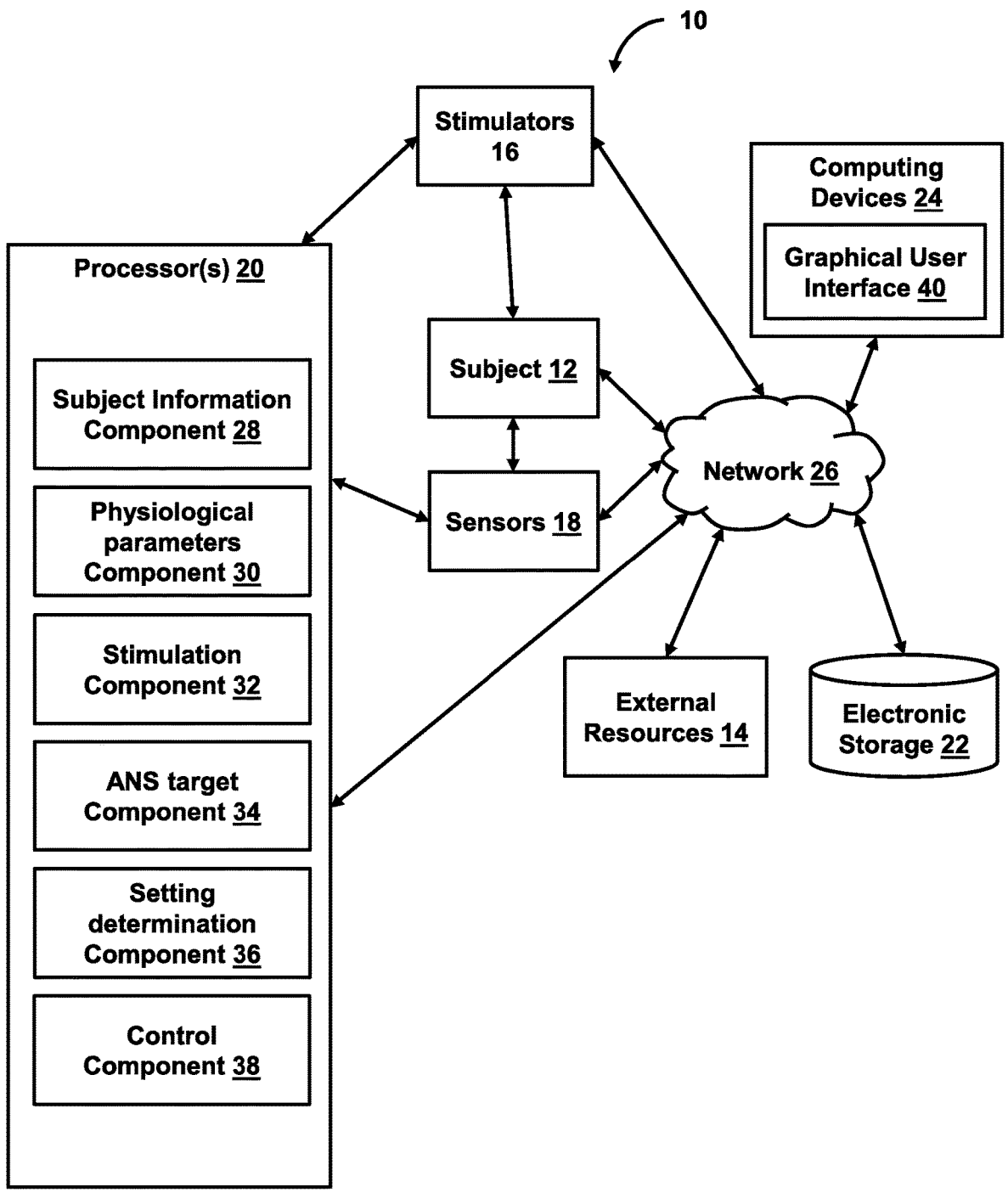
FIG. 1 is a schematic illustration of a system for providing sensory stimulation to facilitate recovery, in accordance with one or more embodiments.

As used herein, the singular form of "a," "an," and "the" include plural references unless the context clearly dictates otherwise. As used herein, the term "or" means "and/or" unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The autonomic nervous system (ANS) is a complex network that controls most of the homeostatic mechanisms in the human body. It consists of the sympathetic and the parasympathetic nervous systems, or more commonly known as the "fight or flight" and the "rest and digest" responses of the body, respectively. The parasympathetic nervous system (PNS) helps produce a state of equilibrium in the body, whereas, the sympathetic nervous system (SNS) prepares the body for a fight response. Methods to influence PNS/SNS activity using pharmacological intervention, sensory stimulation, or biofeedback are known. However, non-pharmacological interventions are preferred to pharmacological interventions due to side-effects associated with the latter. Sensory stimulation is preferred to biofeedback because the former requires a lower level of user engagement compared to the latter. However, adjusting the parameters of the vibratory stimulation to achieve a desired autonomic state is usually done empirically (trial and error), based on subjective preferences, or by copying settings that work for other users. The solutions of the present disclosure overcome these deficiencies in prior art systems.

System 10 (described in FIG. 1), is configured to provide sensory stimulation to a subject. In some embodiments, system 10 may provide stimulation to facilitate recovery (e.g., after exercise or after a period of high SNS/PNS ratio). In some embodiments, system 10 is configured to increase sympathetic activity, based on physical activity (exercising), and provide monitoring of heart-rate recovery (e.g. lowering of heart-rate) under different stimulation settings to determine an optimal setting to promote parasympathetic activity and/or inhibit sympathetic activity. In some embodiments, system 10 allows for accelerating post-exercise physical recovery. In some embodiments, system 10 is configured to apply vibratory stimulation to facilitate heart-rate recovery. In some embodiments, system 10 is configured to use heart-rate decrease to optimize vibration settings. In some embodiments, system 10 is configured to monitor cardiac activity pre and post-exercising to track recovery of heart-rate and heart-rate variability parameters associated with a set of candidate vibration settings. Characterizing the recovery dynamics associated with each candidate setting, allows for ranking the candidate settings based on their influence on autonomic activity. In some embodiments, system 10, is configured to recommend an optimal setting (e.g., based on the previously tested settings or based on reference historic data from the same user or a set of similar users) to the user according to a pre-defined criterion that depends on the monitoring of the physiological metric.

In some embodiments, system 10 comprises one or more of stimulator(s) 16, sensor(s) 18, a processor 20, electronic storage 22, client computing platform(s) 24, a network 26, and/or other components. In FIG. 1, stimulator(s) 16, sensor(s) 18, processor 20, electronic storage 22, and client computing platform(s) 24 are shown as separate entities. In some embodiments, some and/or all of the components of system 10 and/or other components may be grouped into one or more singular devices (e.g., a wearable device or other user device). In some embodiments, a wearable device may include a housing, one or more sensors (e.g., sensors 18), processors (e.g., processors 20), stimulators (e.g., stimulators 16), or other components. One or more sensors, processors, stimulators, and other components of the wearable device, may be housed within or outside of the housing. Such sensors, processors, stimulators, and other components of the wearable device may communicate with one another via wired or wireless connections. It should be noted that, although some embodiments are described herein with respect to a wearable device performing certain operations, one or more such operations may be performed by one or more other components (e.g., one or more servers, client devices, etc.). As an example, such other components (e.g., one or more servers, client devices, etc.) may include one or more processor components that are the same as or similar to subsystems components 28-38.

Sensor(s) 18 is configured to generate output signals conveying information related to one or more physiological parameters of subject 12. In some embodiments, the physiological parameters of the subject may include one or more of heart rate, heart rate variability, microvascular blood volume, galvanic skin resistance, brain activity, and/or other physiological parameters. In some embodiments, sensor(s) 18 may generate an output signals related to a heart rate of subject 12 (e.g., sensor(s) 18 may be a heart rate sensor located on the chest of subject 12, and/or be configured as a bracelet on a wrist of subject 12, and/or be located on another limb of subject 12). In some embodiments, the one or more sensor(s) may include one or more of an electrocardiogram (ECG), a photoplethysmograph (PPG), an electroencephalogram (EEG), a galvanic skin resistance (GSR) sensor, and/or other sensors. In some embodiments, sensor(s) 18 may include a pulse oximeter, a movement sensor, an accelerometer, a blood pressure sensor, an actimetry sensor, a camera, a respiration of subject 12, and/or other sensors configured for monitoring the subject state. Although sensor(s) 18 is illustrated at a single location near subject 12, this is not intended to be limiting. Sensor(s) 18 may include sensors disposed in a plurality of locations, such as for example, coupled (in a removable manner) with clothing of subject 12, worn by subject 12 (e.g., as wristband, a headband etc.), positioned to point at subject 12 (e.g., a camera), and/or in other locations.

In some embodiments, sensor(s) 18 may be included in a wearable device. The wearable device may be any device that is worn, or that is in full or partial contact with any body parts of the subject. In some embodiments, the wearable device may be in the form of a wristband. In some embodiments, wearable device may be configured to generate output signals conveying information related to heart rate, heart rate variability, microvascular blood volume, galvanic skin resistance, alpha power, beta power, brain activity, and/or other physiological parameters. The output signals may be transmitted to a computing device (within or outside of the wearable device) wirelessly and/or via wires. In some embodiments, some or all components of system 10 may be included in a wearable device (e.g., the wristband).

Stimulator(s) 16 is configured to provide stimulation to subject 12. In some embodiments, stimulator(s) may be configured to provide stimulation to the subject based on one or more output signals from sensor(s) 18. In some embodiments, stimulator(s) 16 may be configured to provide stimulation based on one or more stimulation parameters. In some embodiments, the one or more parameters of the stimulator(s) 16 include timing, duration, time interval, intensity, volume, frequency, magnitude, and/or type of stimulation etc. In some embodiments, the one or more parameters may be defined by one or more components of system 10 (as explained below). In some embodiments, the one or more stimulation parameters may be defined by a user (e.g., subject 12), a provider (e.g., healthcare provider), manufacturer, etc. In some embodiments, stimulator(s) 16 may be configured to provide stimulation based on pre-set parameters. For example, the pre-set based on previous stimulation provided to the subject, and/or based on similarities with other subjects. Stimulator(s) 16 may be configured to provide stimulation to subject 12 prior, during, and/or after physical activity.

In some embodiments, stimulation provided to the subject may be peripheral stimulation (e.g., sensory, electric, magnetic, etc.). In some embodiments, other types of stimulation may be considered. In some embodiments, stimulator(s) 16 may be configured to provide vibratory stimulation. Vibratory stimulation in some embodiments, may be easy-to-apply and effective in influencing activity of the ANS. In some embodiments, vibration stimulation may be used to increase parasympathetic activity or decrease sympathetic activity to lower stress, lower heart rate, facilitate sleep, and/or promote relaxation. In some embodiments, vibratory stimulation may include bilateral alternating stimulation tactile (BLAST). In some embodiments, stimulation provided to the subject may comprise haptic stimulation, auditory stimulation, light stimulation, electrical stimulation, magnetic stimulation, visual stimulation, olfactory stimulation, and/or other type of stimulation. Examples of stimulator(s) 16 may include one or more of vibratory stimulator, a coil generating a magnetic field to directly stimulate the brain's cortex, light generators, a fragrance dispenser, a music player, a tone generator, a collection of electrodes on the scalp of subject 12, and/or other stimulators.

In some embodiments, one or more parameters of the stimulator(s) 16 (e.g., type of stimulation, timing, duration, time interval, intensity, volume, frequency, etc.) may be adjusted. For example, based on output signals from sensor(s) 18, adjustments to one or more parameters of the stimulator(s) may be based on feedback from one or more component of system 10, information from individual subjects, information from individual users (e.g., healthcare professionals, caregivers, etc.), manufacturer settings, and/or other information. For example, one or more parameters of the stimulation may be adjusted between upper and lower thresholds. The upper and lower thresholds for the stimulation parameters may be determined for each subject based on previous stimulation interventions, or may be based on similarities between the subject and one or more subjects having one or more similarities with the subject (e.g., brain activity, demographic information, vital sign information, medical/health condition information, treatment history information, similar desired outcome, and/or other similarities.)

For example, in one embodiment, the stimulator (16) is a vibratory stimulator (such as a piezoelectric stimulator or coil-type stimulator), which generates stimulation in the form of vibration. The vibratory stimulation has one or more stimulation parameters. The stimulation parameters include timing, duration, time interval, intensity, volume, frequency, and/or magnitude of the vibrations. In one or more embodiments, the physiological parameters include a heart rate of the subject as measured by the one or more sensors (18), such as a heart rate monitor. The one or more processors (e.g., processors 20 described below) may be configured to adjust output from the vibratory stimulator based on the sensed heart rate. In some embodiments, the one or more processors may iteratively and/or sequentially change one or more of the timing, duration, time interval, intensity, volume, frequency, and/or magnitude of the vibrations in a manner to most effectively reduce the measured heart rate of the user. In some embodiments, stimulator(s) 16 may be included in a wearable device. The wearable device may be any device that is worn, or that is in full or partial contact with any body parts of the subject. In some embodiments, the wearable device may be in the form of a wristband.

Processor 20 is configured to provide information processing capabilities in system 10. As such, processor 20 may include one or more of a digital processor, an analog processor, and a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may include a plurality of processing units. These processing units may be physically located within the same device (e.g., a server), or processor 20 may represent processing functionality of a plurality of devices operating in coordination (e.g., one or more servers, one or more computing devices 24 associated with users, a medical device, stimulator(s) 16, sensor(s) 18, a piece of a hospital equipment, devices that are part of external resources 14, electronic storage 22, and/or other devices.)

As shown in FIG. 1, processor 20 is configured to execute one or more computer program components. The one or more computer program components may comprise one or more of a subject information component 28, a physiological parameters component 30, a stimulation component 32, an ANS target component 34, an optimum setting determination component 36, a control component 38, and/or other components. Processor 20 may be configured to execute components 28, 30, 32, 34, 36, 38 and/or other components by software; hardware; firmware; some combination of software, hardware, and/or firmware; and/or other mechanisms for configuring processing capabilities on processor 20.

It should be appreciated that although components 28, 30, 32, 34, 36, and 38 are illustrated in FIG. 1 as being co-located within a single processing unit, in embodiments in which processor 20 comprises multiple processing units, one or more of components 28, 30, 32, 34, 36, 38, and/or other components may be located remotely from the other components. The description of the functionality provided by the different components 28, 30, 32, 34, 36, 38 and/or other components described below is for illustrative purposes, and is not intended to be limiting, as any of components 28, 30, 32, 34, 36, and/or 38 may provide more or less functionality than is described. For example, one or more of components 28, 30, 32, 34, 36, and/or 38 may be eliminated, and some or all of its functionality may be provided by other components 28, 30, 32, 34, 36, and/or 38. As another example, processor 20 may be configured to execute one or more additional components that may perform some or all of the functionality attributed below to one of components 28, 30, 32, 34, 36, and/or 38.

Subject information component 28, in some embodiments, may be configured to determine (and/or obtain) information related to subject 12. In some embodiments, information related to subject 12 may include biographical information. For example, biographical information may include demographic information (e.g., gender, ethnicity, age, etc.), vital sign information (e.g., weight, BMI, etc.), medical/health condition information (e.g., a disease type, severity of the disease, stage of the disease, categorization of the disease, symptoms, behaviors, readmission, relapse, etc.), treatment history information (e.g., type of treatments, length of treatment, current and past medications, etc.), and/or other information. In some embodiments, subject information component 28 may include feedback from previous stimulations, previous physical activity information, and/or previous physiological information (e.g., heart rate, HRV, brain activity, etc.)

In some embodiments, subject information component 28 may be configured to determine (and/or obtain) information related other subjects. For example, subjects with similar demographic information, vital sign information, medical/health condition information, treatment history information, similar desired outcome (e.g., from sensory simulation), and/or other similarities with subject 12. It should be noted that the subject information described above is not intended to be limiting. A large number of information related to subjects may exist and may be used with system 10 in accordance with some embodiments. For example, users may choose to customize system 10 and include any type of subject data they deem relevant.

In some embodiments, subject information component 28 may be configured to obtain/extract information from one or more databases (e.g., electronic storage shown 22 in FIG. 1). In some embodiments, different databases may contain different information about subject 12 and/or about other subjects (e.g. similar to subject 12). In some embodiments, some databases may be associated with specific subject information (e.g., a medical condition, a demographic characteristic, a treatment, a therapy, a medical device used, a vital sign information, etc.) In some embodiments, subject information component 28 may be configured to obtain/extract the subject information from external resources 14 (e.g., one or more external databases included in external resources 14), electronic storage 22 included in system 10, one or more medical devices, and/or other sources of information.

Physiological parameters component 30 may be configured to determine (and/or obtain) one or more physiological parameters related to subject 12. In some embodiments, one or more physiological parameters is determined based on output signals from sensor(s) 18. In some embodiments, the one or more physiological parameters include a degree of parasympathetic activity. In some embodiments, a degree of parasympathetic activity may be useful in quantifying the subject's recovery time and/or propensity to relax. In some embodiments, a degree of parasympathetic activity may be determined based on cardiac activity of the subject (e.g., ECG, and/or PPG). In some embodiments, the one or more physiological parameters includes heart rate of the subject.

In some embodiments, the one or more physiological parameters may include heart rate variability HRV. HRV is the amount of variability in the time intervals between adjacent heartbeats, i.e. RR. Typically, NN intervals, i.e. RR intervals from which artifacts have been removed are used for further analysis. In some embodiments, one or more physiological parameters may include, microvascular blood volume, galvanic skin resistance, alpha power, beta power, brain activity, and/or other physiological parameters.

In some embodiments, the one or more physiological parameters may be determined before, during, and/or after a physical activity. For example, in some embodiments, the one or more physiological parameters may be determined before the subjects performs a physical activity. To increase the heart rate of the subject, the subject may be asked to perform a physical activity. In some embodiments, characteristics of the exercise (e.g., the type, duration, and/or intensity) may be determined based on the subject (e.g., the subject demographic, fitness level, etc.). In some embodiments, characteristics of the exercise may be determined based on a HR target (e.g., increasing HR by 20 beats-per-minute compared to HR prior to starting the exercise session.) In some embodiments, heart-rate is monitored during the exercise period and the system notifies the user when the target rate has been reached and the exercise period can be stopped. In some embodiments, after the exercise period has ended, HR during the recovery period is monitored and the decay in HR after a given reference-duration into the recovery period is compared to a HR reference-value (as explained below).

Stimulation component 32 is configured to determine one or more parameters of stimulation to be delivered to the subject. In some embodiments, the one or more stimulation parameters may include (type, duration, timing, time interval, intensity, volume, frequency, etc.) In some embodiments, stimulation component 32 is configured to determine one or more parameters of the stimulation based on the one or more output signals from sensor(s) and/or based on one or more physiological parameters of the subject. In some embodiments, the one or more stimulation parameters may be defined by a user (e.g., subject 12), a provider (e.g., healthcare provider), manufacturer, etc. In some embodiments, stimulator(s) 16 may be configured to provide stimulation based on previously administered stimulation (For example, based on previous stimulation provided to the subject, and/or based on similarities with other subjects.) In some embodiments, stimulation component 32 may determine a timing of the stimulation (e.g., prior, during, and/or after a physical activity).

ANS activity target component 34 is configured to determine (and/or obtain) an ANS activity target. In some embodiments, the target can be specified as an absolute (e.g. a level of heart rate variability) or relative (e.g. lower sympathetic activity) target. In some embodiments, the ANS activity target component 34 may be configured to determine one or more physiological targets. For example, the one or more physiological targets may correspond to one or more ANS activity targets. In some embodiments, ANS activity target may determine a heart rate target, a HRV target, a brain activity target, an alpha power target, a beta power target, a microvascular blood volume target, a galvanic skin resistance target and/or other physiological parameters targets. In some embodiments, ANS target component 34 is configured to determine (and/or obtain) an ANS activity target (and/or one or more physiological targets) that facilitates recovery, relaxation, and/or sleep. In some embodiments, the ANS activity target (and/or one or more physiological targets) may be obtained from a data base within or outside system 10. For example, in some embodiments, the ANS activity target may be obtained based on previously determined ANS activity corresponding to the subject. In some embodiments, the ANS activity target may be determined based on one or more ANS activity corresponding to other subjects (e.g., subjects similar to subject 12). In some embodiments, the ANS activity target may be pre-determined (e.g., by a provider, user, manufacturer, etc.) In some embodiments, the ANS activity target may be determined based on information conveyed by the output signals of sensor(s) 18. For example, ANS activity target component 34 may be configured to determine ANS activity target based on changes in autonomic activity preceding, during, or after physical activity.

Figure 2:
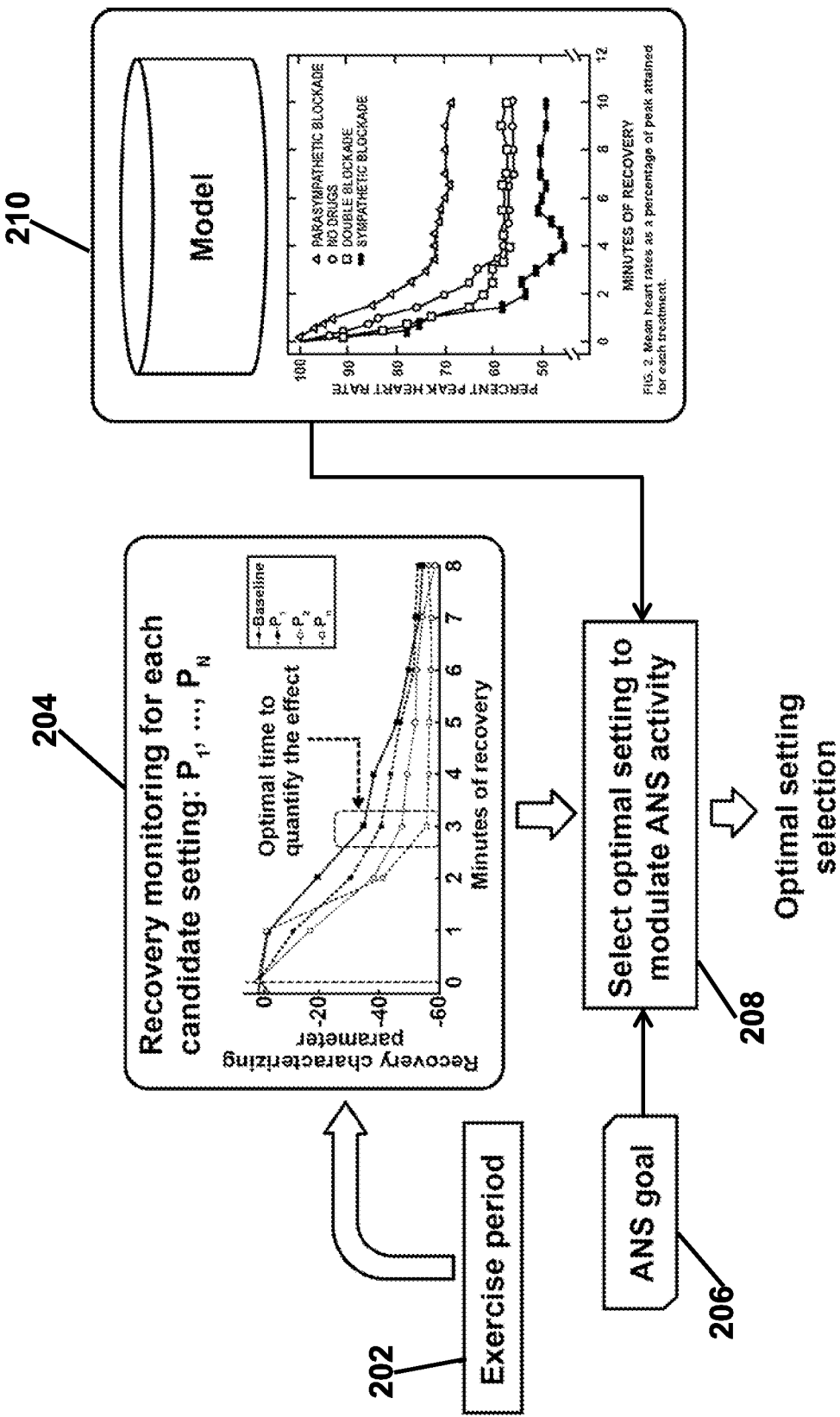
FIG. 2 illustrates example operations performed by a system for providing sensory stimulation to facilitate recovery, in accordance with one or more embodiments.

Setting determination component 36 configured to determine one or more stimulation parameters of sensory stimulation to be delivered to the subject. In some embodiments, the one or more stimulation parameters may be based on the heart rate target (e.g., determined by the ANS activity target). In some embodiments, the one or more stimulation parameters may be based on the one or more physiological parameters determined by physiological parameters component 30. The one or more physiological parameters may include heart rate, heart rate variability, microvascular blood volume, galvanic skin resistance, alpha power, beta power, brain activity, and/or other physiological parameters. In some embodiments, stimulations parameters may be determined based on data from previous stimulation sessions of the subject. For example, obtained or extracted from a database containing historical information about previous stimulation session of the subject (e.g., electronic storage 22). In some embodiments, one or more settings of previous stimulation sessions may be used as a baseline. In some embodiments, for example, the setting determination component may be configured to use one or more settings from the historical settings that had the least recovery time. For example, the stimulator may be configured to provide the baseline stimulation settings and adjust the stimulation settings based on the subjects response (time to recovery). In some embodiments, the new adjusted stimulation parameters may be considered the new baseline for subsequent stimulation sessions. In some embodiments, stimulations parameters may be determined based on data from previous stimulation sessions of other subjects. For example, obtained or extracted from a database containing historical information about previous stimulation sessions of other subjects (e.g., electronic storage 22). In some embodiments, the other subjects may be subjects who are similar to the subject. For example, subjects having similar demographic information, vital sign information, medical/health condition information, treatment history information, similar desired outcome (e.g., from sensory simulation), and/or other similarities with subject 12. FIG. 2 (described below) shows an example of determination of the one or more stimulation parameters of sensory stimulation to be delivered to the subject.

FIG. 2 illustrates example operations performed by a system for providing sensory stimulation to facilitate recovery, in accordance with one or more embodiments. For example, operations performed by system 10 described above. In some embodiments, system 10 may be configured to determine optimal stimulation settings to influence the ANS. In some embodiments, system 10 may be configured to determine optimal stimulation settings to obtain an accelerated recovery (e.g., post-exercise recovery). In some embodiments, the subject may be requested to perform physical activity to increase the sympathetic activity. After an exercise period 202, the heart-rate recovery 204 (e.g. lowering of heart-rate) is subsequently monitored under different vibratory stimulation settings to determine the most optimal setting to promote parasympathetic activity or to inhibit sympathetic activity under different vibratory stimulation settings. The heart rate recovery 204 is described in more detail in FIG. 3-4 (below).

In the example of FIG. 2, a set of candidate vibration settings {Pn: n=1, . . . , N} are considered to modulate the ANS activity according to a desired target ANS activity goal 206. In some embodiments, the ANS goal 206 can be specified as an absolute (e.g. a level of heart rate variability) or relative (e.g. lower sympathetic activity) target. To determine the optimal vibration settings {Pn} 208 to meet the desired goal, the user performs a given physical activity (exercising) which acutely increases heart-rate (e.g. running). The exercising period 202 lasts for a pre-defined duration (e.g. 5 minutes) or until a target heart-rate is reached. In some embodiment, the exercise period increases heart-rate (HR) by 20 beats-per-minute compared to HR prior to starting the exercise session. For example, depending on the user demographic characteristics, this can be accomplished by jogging for 5 minutes. In some embodiments, the heart-rate is monitored during the exercise period and the system notifies the user when the target rate has been reached and the exercise period 202 can be stopped. The heart rate can be monitored using one or more sensors 18 described above (e.g., an ECG or PPG measurement device).

In some embodiments, during the recovery period 204 (e.g., after exercising), an index of recovery (e.g. heart-rate) is continuously monitored and is compared to a literature-based model 210. Model 210 shows that increase in heart rate that accompanies exercise is due in part to a reduction in vagal, i.e. parasympathetic tone. Drug-based sympathetic (parasympathetic) nervous system blockade accelerates (slows-down) heart-rate recovery after exercising compared to a no-drugs condition. In some embodiments, a given setting {Pn} can be qualified as SNS or PNS promotor depending on whether its recovery curve is below or above a baseline curve (described in FIG. 3). Depending on the nature of the ANS target 206, a particular vibration setting is selected. After the exercise period has ended, the heart-rate during the recovery period is monitored and the decay in heart-rate after a given reference-duration into the recovery period is compared to a reference-value. In some embodiments, the reference-duration is 1-minute long based on the experimental results summarized in FIGS. 3-4.

Figure 3:
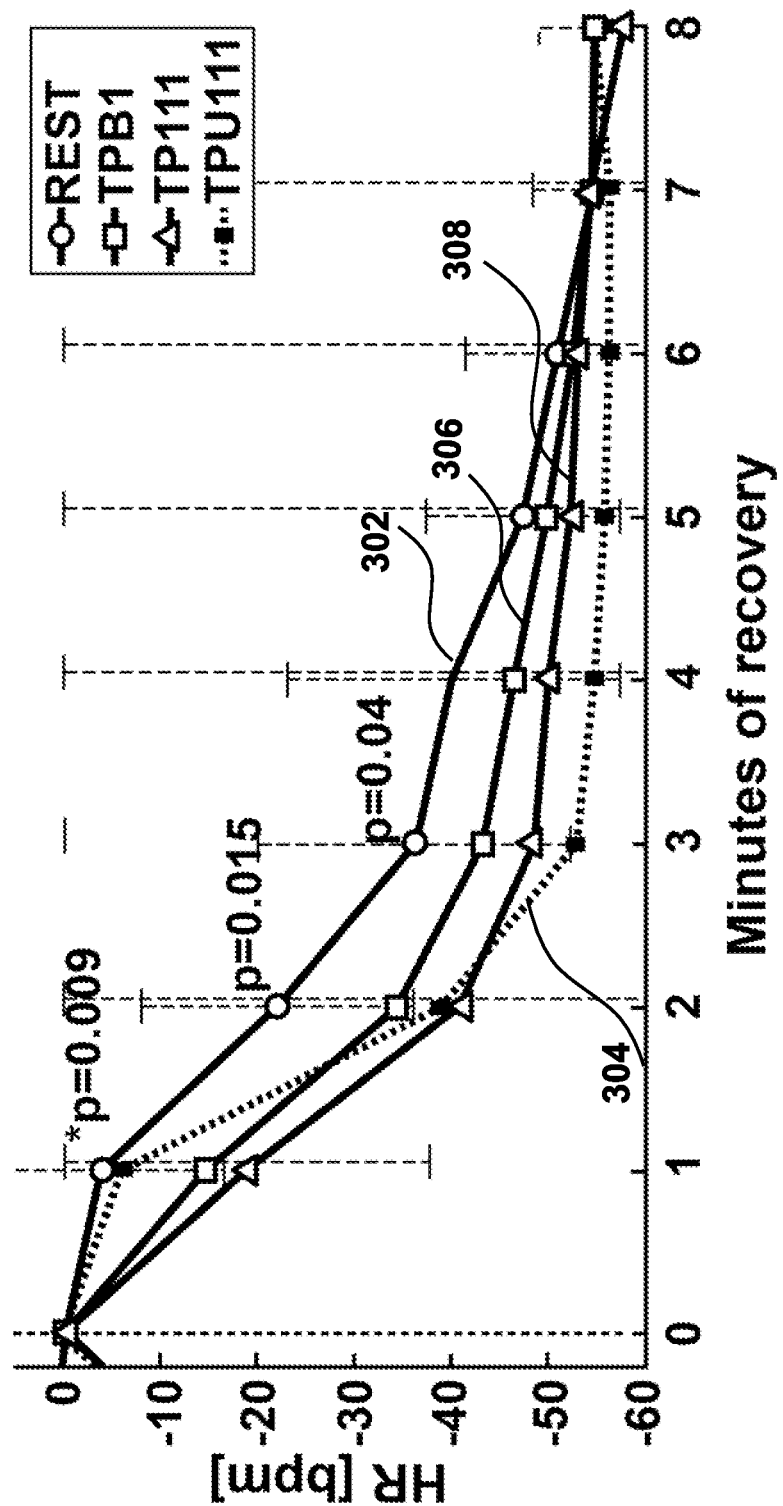
FIG. 3 illustrates an example optimization of heart-rate recovery using vibratory stimulation, in accordance with one or more embodiments.

FIG. 3 describes an example optimization of heart-rate recovery using vibratory stimulation according to one or more embodiments. In the example of FIG. 3, the reference-value, 302 is the decay in heart-rate when no intervention is applied. The reference-value 302 can be from the same user if recovery heart-rate from a prior baseline session exists or from similar users whose data is stored in a database. In some embodiments, the notion of similarity is determined based on demographic characteristics (age and gender). In some embodiments, similar users may have similar demographic information, vital sign information, medical/health condition information, treatment history information, similar desired outcome (e.g., from sensory simulation), and/or other similarities with subject 12. An experiment was conducted where six subjects participated in an experiment where they performed an exercise session lasting for ten minutes followed by a 10-minute recovery period. During both, the exercise and recovery periods, the user's heart-rate was monitored using an ECG recording device. During the recovery period, four conditions were tested: 1) Rest or baseline during which subjects simply rested after the exercise period and 2-4) rest while simultaneously wearing watch-like vibration stimulation delivery devices (Touchpoints™) in both wrists. Condition 2 TPB1 corresponds to the basic-2 setting (bilateral alternating stimulation-tactile) in the Touchpoints device, Condition 3 TP111 corresponds to the original-111 setting (bilateral alternating stimulation-tactile) in the Touchpoints device, and Condition 4 TPU111 is identical to 3) but only a single watch is used on the non-dominant hand.

The average recovery curves (302 for the rest condition, 304 for the TP111 condition, 306 for the TPB1 condition, and 308 for the TPU111 condition) for each condition are shown in FIG. 3. For each curve 302, 304, 306, and 308 time 0 indicates the beginning of the recovery period and, for ease of interpretation, the heart-rate was normalized to 0 at time 0. The rest condition 302 was taken as reference. Statistical significance was tested at each time point (in minutes) between each condition and the rest condition. The setting TP111 304 resulted in statistically significant differences. The p-value and standard deviations (shown as vertical lines) for the Rest and TP111 conditions are shown in FIG. 3. For example, as shown in FIG. 3, at 1 minute recovery time, the p-value is 0.009. At 2 minutes recovery time, the p-value is 0.015. At 3 minutes recovery time, the p-value is 0.04.

Figure 4:
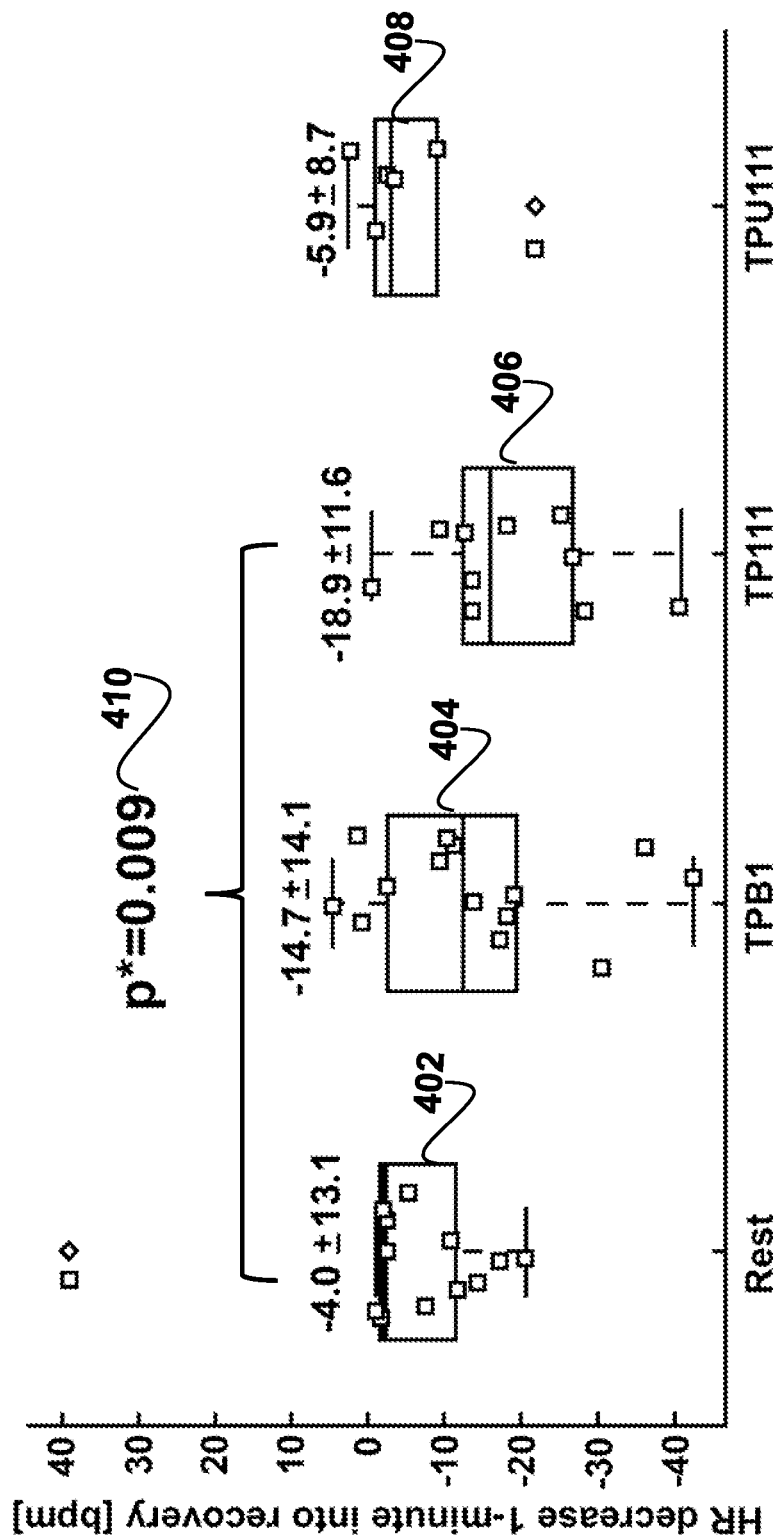
FIG. 4 illustrates a comparison between conditions after an exercise period has ended, in accordance with one or more embodiments.

Statistically significant differences were already found after a minute into the recovery period. FIG. 4 illustrates a comparison between conditions a minute after the exercise period has ended. The boxplots in FIG. 4 show the data distribution using boxplots for each condition. Boxplot 402 is the data distribution of the Rest condition. Boxplot 404 is the data distribution of the TPB1 condition. Boxplot 406 is the data distribution of the TP111 condition. Boxplot 408 is the data distribution of the TPU111 condition. In this particular example, TP111 setting appears to be the most effective in lowering heart-rate during the recovery period. The p-value for the Rest and TP111 conditions 410 is 0.009. Given that heart-rate reduction during recovery is hypothesized to result from vagal activation, the TP111 setting is selected as the preferred setting for parasympathetic activation. Other experiments (daytime and evening relaxation; relaxation after performing the Stroop task) on the same subjects suggested that TP111 setting was effective in increasing heart-rate variability which is also a correlate of increased parasympathetic activity. Heart-rate after exercising decreases (i.e. recovers) significantly faster when using vibration with settings TP111.

Returning to FIG. 1, control component 38 is configured to control stimulator(s) 16 to provide stimulation to subject 12. In some embodiments, control component 38 may be configured to cause stimulator(s) 16 to provide stimulation, based on the one or more stimulation parameters determined by Setting determination component 36. In some embodiments, control component 38 may be configured to control stimulator(s) 16 to adjust the stimulation in real-time (or near real time) based on one or more signals from sensor(s) 18 (e.g., related to physiological parameters.) In some embodiments, control component 38 may be configured to automatically deliver a type of vibratory stimulation. This can be accomplished by considering a database of type of stimulation versus autonomic effect. In some embodiments, control component may be configured to adjust stimulation between an upper threshold and a lower threshold. The upper thresholds and a lower thresholds may be determined based on information related to subject 12, information related to subjects similar to subject 12, and/or based on other parameters determined by a user (e.g., healthcare professional, caregiver, etc.), and/or one or more components within or outside of system 10. In some embodiments, control component 38 may be configured to control stimulator(s) 16 to provide stimulation to subject 12 prior, during, and/or after an exercise session, and/or at other times.

In some embodiments, as shown in FIG. 1, system 10 may include one or more of external resources 14, electronic storage 22, client computing platform(s) 24, network 26, and/or other components, all being communicatively coupled via a network 26.

External resources 14 include sources of patient and/or other information. In some embodiments, external resources 14 include sources of patient and/or other information, such as databases, websites, etc., external entities participating with system 10 (e.g., a medical records system of a healthcare provider that stores medical history information for populations of patients), one or more servers outside of system 10, a network (e.g., the internet), electronic storage, equipment related to Wi-Fi technology, equipment related to Bluetooth® technology, data entry devices, sensors, scanners, and/or other resources. In some embodiments, some or all of the functionality attributed herein to external resources 14 may be provided by resources included in system 10. External resources 14 may be configured to communicate with processor 20, computing devices 24, electronic storage 22, and/or other components of system 10 via wired and/or wireless connections, via a network (e.g., a local area network and/or the internet), via cellular technology, via Wi-Fi technology, and/or via other resources.

Electronic storage 22 includes electronic storage media that electronically stores information. The electronic storage media of electronic storage 22 may include one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may be (in whole or in part) a separate component within system 10, or electronic storage 22 may be provided (in whole or in part) integrally with one or more other components of system 10 (e.g., computing devices 24, processor 20, etc.). In some embodiments, electronic storage 22 may be located in a server together with processor 20, in a server that is part of external resources 14, in a computing device 24, and/or in other locations. Electronic storage 22 may include one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information determined by processor 20, information received via a computing device 24 and/or graphical user interface 40 and/or other external computing systems, information received from external resources 14, stimulators 16, sensors 18, and/or other information that enables system 10 to function as described herein.

Client computing platform(s) 24 is configured to provide an interface between system 10 and subject 12, and/or other users through which subject 12 and/or other users may provide information to and receive information from system 10. For example, client computing platform(s) 24 may display a representation of the output signal from sensors 18 (e.g., an EEG, 2D/3D images, video, audio, text, etc.) to a user. This enables data, cues, results, instructions, and/or any other communicable items, collectively referred to as "information," to be communicated between a user (e.g., subject 12, a doctor, a caregiver, and/or other users) and one or more of stimulator(s) 16, processor 20, electronic storage 22, and/or other components of system 10.

Examples of interface devices suitable for inclusion in client computing platform(s) 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, client computing platform(s) 24 comprises a plurality of separate interfaces. In some embodiments, client computing platform(s) 24 comprises at least one interface that is provided integrally with processor 20, stimulator(s) 16, sensor(s) 18, and/or other components of system 10.

Computing devices 24 are configured to provide interfaces between caregivers (e.g., doctors, nurses, friends, family members, etc.), patients, and/or other users, and system 10. In some embodiments, individual computing devices 24 are, and/or are included, in desktop computers, laptop computers, tablet computers, smartphones, and/or other computing devices associated with individual caregivers, patients, and/or other users. In some embodiments, individual computing devices 24 are, and/or are included, in equipment used in hospitals, doctor's offices, and/or other medical facilities to patients; test equipment; equipment for treating patients; data entry equipment; and/or other devices. Computing devices 24 are configured to provide information to, and/or receive information from, the caregivers, patients, and/or other users. For example, computing devices 24 are configured to present a graphical user interface 40 to the caregivers to facilitate display representations of the data analysis, and/or other information. In some embodiments, graphical user interface 40 includes a plurality of separate interfaces associated with computing devices 24, processor 20 and/or other components of system 10; multiple views and/or fields configured to convey information to and/or receive information from caregivers, patients, and/or other users; and/or other interfaces.

In some embodiments, computing devices 24 are configured to provide graphical user interface 40, processing capabilities, databases, and/or electronic storage to system 10. As such, computing devices 24 may include processors 20, electronic storage 22, external resources 14, and/or other components of system 10. In some embodiments, computing devices 24 are connected to a network (e.g., the internet). In some embodiments, computing devices 24 do not include processors 20, electronic storage 22, external resources 14, and/or other components of system 10, but instead communicate with these components via the network. The connection to the network may be wireless or wired. For example, processor 20 may be located in a remote server and may wirelessly cause display of graphical user interface 40 to the caregivers on computing devices 24. As described above, in some embodiments, an individual computing device 24 is a laptop, a personal computer, a smartphone, a tablet computer, and/or other computing devices. Examples of interface devices suitable for inclusion in an individual computing device 24 include a touch screen, a keypad, touch-sensitive and/or physical buttons, switches, a keyboard, knobs, levers, a display, speakers, a microphone, an indicator light, an audible alarm, a printer, and/or other interface devices. The present disclosure also contemplates that an individual computing device 24 includes a removable storage interface. In this example, information may be loaded into a computing device 24 from removable storage (e.g., a smart card, a flash drive, a removable disk, etc.) that enables the caregivers, patients, and/or other users to customize the implementation of computing devices 24. Other exemplary input devices and techniques adapted for use with computing devices 24 include, but are not limited to, an RS-232 port, an RF link, an IR link, a modem (telephone, cable, etc.), and/or other devices.

The network 26 may include the Internet and/or other networks, such as local area networks, cellular networks, Intranets, near field communication, frequency (RF) link, Bluetooth™, Wi-Fi™, and/or any type(s) of wired or wireless network(s). Such examples are not intended to be limiting, and the scope of this disclosure includes embodiments in which external resources 14, stimulator(s) 16, sensor(s) 18, processor(s) 20, electronic storage 22, and/or client computing platform(s) 24 are operatively linked via some other communication media.

Figure 5:
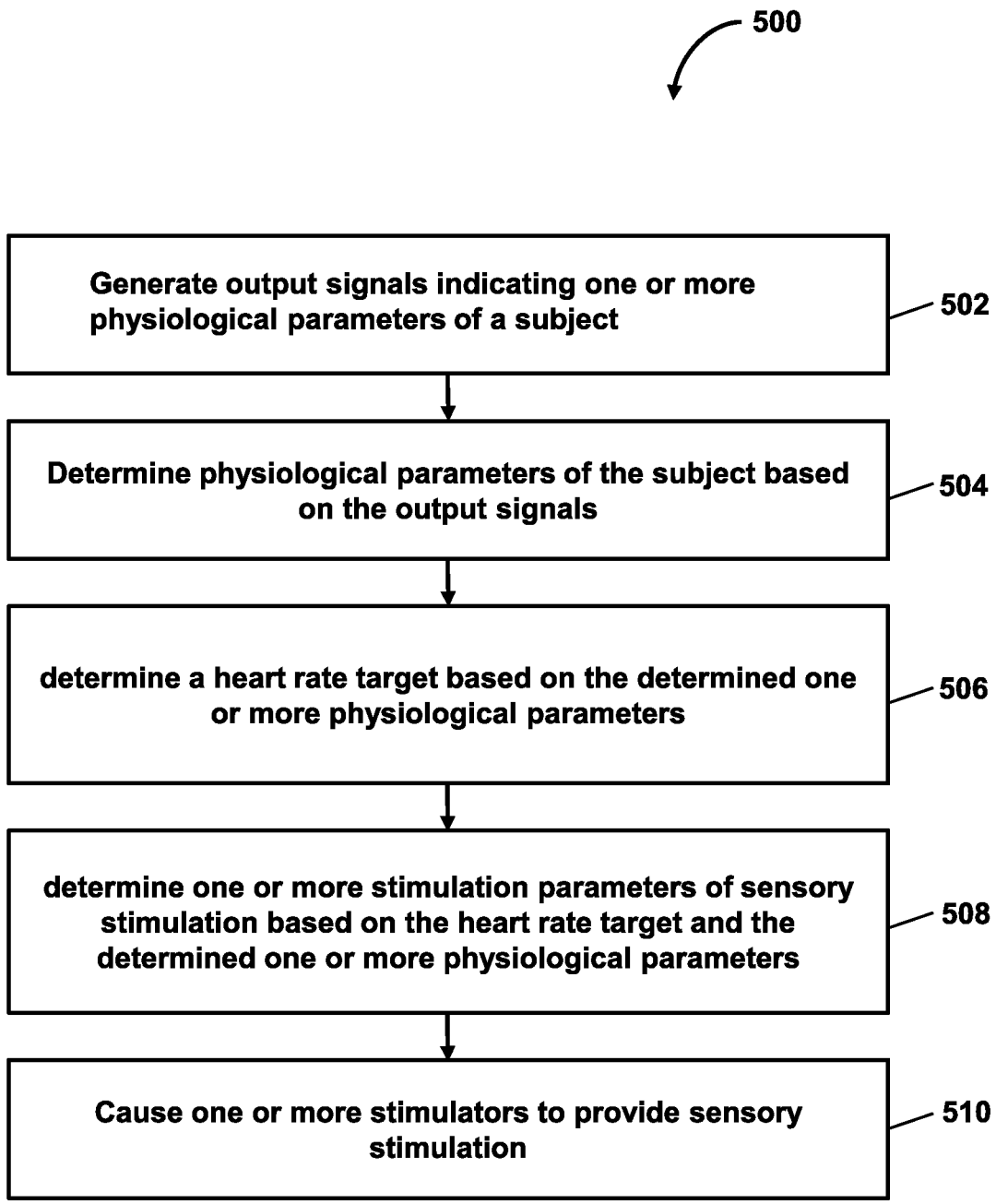
FIG. 5 illustrates a method for providing sensory stimulation to facilitate recovery, in accordance with one or more embodiments.

FIG. 5 illustrates a method 500 for providing sensory stimulation to facilitate recovery. The system comprises one or more sensors, one or more stimulators, one or more physical computer processors, and/or other components. The one or more processors are configured to execute one or more computer program components. The one or more computer program components may comprise a subject information component 28, a physiological parameters component 30, a stimulation component 32, an ANS target component 34, an optimum setting determination component 36, a control component 38, and/or other components. The operations of method 500 presented below are intended to be illustrative. In some embodiments, method 500 may be accomplished with one or more additional operations not described, and/or without one or more of the operations discussed. Additionally, the order in which the operations of method 500 are illustrated in FIG. 5 and described below is not intended to be limiting.

In some embodiments, method 500 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 500 in response to instructions stored electronically on an electronic storage medium. The one or more processing devices may include one or more devices configured through hardware, firmware, and/or software to be specifically designed for execution of one or more of the operations of method 500.

At operation 502, output signals indicating one or more physiological parameters of a subject are generated. In some embodiments, operation 502 is performed by a one or more sensors the same as or similar to sensor (18) (shown in FIG. 1 and described herein).

At operation 504, one or more physiological parameters of the subject are determined based on the output signals. In some embodiments, the one or more physiological parameters indicating a heart rate of the subject. In some embodiments, operation 504 is performed by a physical computer processor the same as or similar to processor(s) 20 (shown in FIG. 1 and described herein).

At operation 506, a heart rate target is determined based on the determined one or more physiological parameters indicating the heart rate of the subject. In some embodiments, the heart rate target is lower than the determined heart rate. In some embodiments, operation 506 is performed by a physical computer processor the same as or similar to processor(s) 20 (shown in FIG. 1 and described herein).

At operation 508, one or more stimulation parameters of sensory stimulation to be delivered to the subject are determined based on the heart rate target and the determined one or more physiological parameters. In some embodiments, operation 508 is performed by a physical computer processor the same as or similar to processor(s) 20 (shown in FIG. 1 and described herein).

At operation 510, the sensory stimulation is delivered to the subject based on the determined one or more stimulation parameters. In some embodiments, operation 510 is performed by a physical computer processor the same as or similar to processor(s) 20 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system for delivering sensory stimulation to a subject, the system comprising:
   one or more sensors configured to generate output signals indicating one or more physiological parameters of a subject;
   a sensory stimulator configured to deliver sensory stimulation to the subject; and
   one or more physical processors operatively connected with the one or more sensors and the sensory stimulator, the one or more physical processors being programmed with computer program instructions which, when executed cause the system to:
      determine one or more physiological parameters of the subject based on the output signals from the one or more sensors, the determined one or more physiological parameters including a heart rate of the subject or a Heart Rate Variability (HRV) of the subject;
      determine, based on the determined one or more physiological parameters of the subject, a heart rate target lower than the determined heart rate or an HRV target higher than the determined HRV;
      determine one or more stimulation parameters of sensory stimulation to be delivered to the subject based on the heart rate target and the determined heart rate of the subject or the HRV target and the determined HRV of the subject;
      cause the sensory stimulator to deliver the sensory stimulation to the subject based on the determined one or more stimulation parameters; and
      monitor heart-rate recovery of the subject after increased sympathetic activity under different sensory stimulation settings to determine the most optimal sensory setting to promote parasympathetic activity and/or to inhibit sympathetic activity under the different sensory stimulation settings.

2. The system of claim 1, wherein the sensory stimulator is configured to deliver vibratory stimulation to the subject.

3. The system of claim 2, wherein the one or more stimulation parameters comprise vibratory stimulation parameters including bilateral alternating stimulation-tactile.

4. The system of claim 1, wherein the determined one or more physiological parameters includes the heart rate of the subject and the determination, based on the determined one or more physiological parameters of the subject, the heart rate target lower than the determined heart rate; and wherein the one or more physical processors are further configured to:
   provide instruction to the subject to start a physical activity;
   responsive to the heart rate of the subject reaching a pre-determined heart rate value,
   cause the stimulator to deliver stimulation to the subject, the stimulation having one or more baseline parameters;
   determine a recovery period for the subject, the recovery period corresponding to a time to reach the heart rate target; and
   determine one or more stimulation parameters of sensory stimulation to be delivered to the subject in subsequent stimulation based on the determined recovery period.

5. The system of claim 1, wherein the one or more physical processors are configured to determine a recovery period for the subject, the recovery period corresponding to a time to reach the heart rate target or the HRV target.

6. The system of claim 1, wherein the one or more physical processors are further configured to:
   obtain stimulation response information from the subject; and
   adjust the one or more stimulation parameters of the sensory stimulation based on the stimulation response.

7. The system of claim 1, wherein the one or more sensors include one or more of an electrocardiogram (ECG), photoplethysmograph (PPG), electroencephalogram (EEG), and/or galvanic skin resistance (GSR) sensor, and wherein the one or more physiological parameters include one or more of alpha power, beta power, and/or skin conductance.

8. A method for delivering sensory stimulation to a subject, the method comprising: generating, with one or more sensors, output signals indicating one or more physiological parameters of a subject;
   determining, with one or more physical processors, one or more physiological parameters of the subject based on the output signals from the one or more sensors, the one or more physiological parameters determined based on the output signals from the one or more sensors including a heart rate of the subject or a Heart Rate Variability (HRV) of the subject;
   determining, based on the one or more physical parameters determined based on the output signals from the one or more sensors, a heart rate target lower than the determined heart rate or an HRV target higher than the determined HRV;

determining, with one or more physical processors, one or more stimulation parameters of sensory stimulation to be delivered to the subject based on the heart rate target and the determined heart rate of the subject or the HRV target and the determined HRV of the subject;

causing, with one or more physical processors, a sensory stimulator to deliver sensory stimulation to the subject based on the determined one or more stimulation parameters; and monitor heart-rate recovery of the subject after increased sympathetic activity under different sensory stimulation settings to determine the most optimal sensory setting to promote parasympathetic activity and/or to inhibit sympathetic activity under the different sensory stimulation settings.

9. The method of claim 8, wherein the sensory stimulator is configured to deliver vibratory stimulation to the subject.

10. The method of claim 9, wherein the one or more stimulation parameters comprise vibratory stimulation parameters including bilateral alternating stimulation-tactile.

11. The method of claim 9, wherein the determined one or more physiological parameters includes the heart rate of the subject and the determining, based on the determined one or more physiological parameters of the subject, the heart rate target lower than the determined heart rate; and wherein the method further comprises:

providing, with one or more physical processors, instruction to the subject to start a physical activity;

responsive to the heart rate of the subject reaching a pre-determined heart rate value, causing, with one or more physical processors, the sensory stimulator to deliver stimulation to the subject, the stimulation having one or more baseline parameters;

determining, with one or more physical processors, a recovery period for the subject, the recovery period corresponding to a time to reach the heart rate target; and determining, with one or more physical processors, one or more stimulation parameters of sensory stimulation to be delivered to the subject in subsequent stimulation based on the determined recovery period.

12. The method of claim 8, further comprising determining a recovery period for the subject, the recovery period corresponding to a time to reach the heart rate target or the HRV target.

13. The method of claim 8, further comprising:
obtaining, with one or more physical processors, stimulation response information from the subject; and
adjusting, with one or more physical processors, the one or more stimulation parameters of the sensory stimulation based on the stimulation response.

14. The method of claim 8, wherein the one or more sensors include one or more of an electrocardiogram (ECG), photoplethysmograph (PPG), electroencephalogram (EEG), and/or galvanic skin resistance (GSR) sensor, and wherein the one or more physiological parameters include one or more of alpha power, beta power, and/or skin conductance.

* * * * *